United States Patent [19]

Braestrup et al.

[11] Patent Number: 4,748,179

[45] Date of Patent: May 31, 1988

[54] β-CARBOLIN-3-CARBOXYLIC ACID DERIVATIVES AND THEIR USE AS BENZODIAZEPINE ANTAGONISTS

[75] Inventors: Claus T. Braestrup; Erling Petersen, both of Glostrup; Tage Honore, Maaloev; Leif H. Jensen, Hellerup, all of Denmark; Dieter Seidelmann, Berlin, Fed. Rep. of Germany

[73] Assignee: Schering Aktiengesellschaft, Berlin and Bergkamen, Fed. Rep. of Germany

[21] Appl. No.: 746,811

[22] Filed: Jun. 20, 1985

Related U.S. Application Data

[63] Continuation of Ser. No. 614,504, May 29, 1984, abandoned.

[30] Foreign Application Priority Data

May 27, 1983 [DK] Denmark ............................ 2402/83

[51] Int. Cl.$^4$ .................. A61K 31/395; A61K 31/40; C07D 471/04
[52] U.S. Cl. ...................................... 514/292; 546/86
[58] Field of Search ........................... 546/86; 514/292

[56] References Cited

U.S. PATENT DOCUMENTS

| | | | |
|---|---|---|---|
| 3,202,667 | 8/1965 | Szuszkovicz et al. | 546/86 |
| 4,371,536 | 2/1983 | Braestrup et al. | 546/86 |
| 4,435,403 | 3/1984 | Braestrup et al. | 546/86 |

FOREIGN PATENT DOCUMENTS 57-4897  1/1982  Japan .................................. 546/86

OTHER PUBLICATIONS

In re Schaumann et al, 197, USPO 5 (CCPA 1978).
L. H. Jensen et al., Bidirectional Effects of Benzodiazeping Receptor Ligands Against Picrotoxin etc., 183-191 (1983).

Primary Examiner—Alan L. Rotman
Assistant Examiner—J. Richter
Attorney, Agent, or Firm—Millen & White

[57] ABSTRACT

β-carbolin-3-carboxylic acid derivatives of the general formula

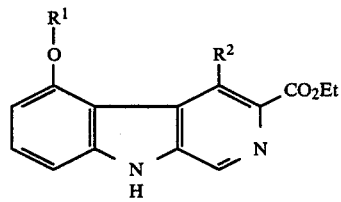

wherein
$R^1$ is methyl, ethyl, n-propyl or iso-propyl, and wherein
$R^2$ is hydrogen, methyl, ethyl, n-propyl or iso-propyl, provided that $R^1$ is not methyl, when $R^2$ is hydrogen, are produced by different methods.

The compounds are useful in psychopharmaceutical preparations, being antagoinists of benzodiazepines.

10 Claims, No Drawings

β-CARBOLIN-3-CARBOXYLIC ACID DERIVATIVES AND THEIR USE AS BENZODIAZEPINE ANTAGONISTS

This is a continuation of application Ser. No. 614,504, filed May 29, 1984, now abandoned.

BACKGROUND OF THE INVENTION

This invention relates to new β-carboline-3-carboxylic acid derivatives and to methods of preparing them. The new compounds are useful in psychopharmaceutical preparations being antagonists of benzodiazepines.

EP published patent application No. 30 254, whose disclosure is incorporated by reference herein, discloses compounds represented by the following generic formula:

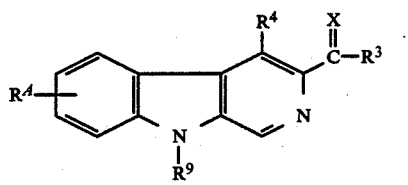

wherein
X is oxygen, sulphur or $NR^{10}$, wherein $R^{10}$ is hydrogen, lower alkyl or cycloalkyl;
$R^3$ is (a) alkoxy, aryloxy or aralkoxy, each optionally substituted with one or more e.g., 1–3, halogen atoms (F, Cl, Br, I), hydroxy groups, $CF_3$ groups, or alkoxy groups or with an amino, dialkylamino or alkoxycarbonyl group; or (b) $NR^{11}R^{12}$, wherein $R^{11}$ and $R^{12}$ are the same or different and each is (i) hydrogen, (ii) hydroxy, (iii) alkyl, (iv) aryl, (v) aralkyl or (vi) cycloalkyl, the latter four (iii–vi) optionally substituted with a hydroxy, a carboxamido, an alkoxycarbonyl, a carboxy, a monosaccharide or a heterocyclic group, or (vii) amino optionally substituted with alkyl, aryl, aralkyl, or cycloalkyl; or wherein $R^{11}$; and $R^{12}$ together with the adjoining nitrogen atom form an optionally substituted 5-, 6- or 7-membered heterocyclic ring; with the proviso that $R^{11}$ and $R^{12}$ cannot both be hydroxy; or wherein X and $R^3$ together represent a single nitrogen atom;
$R^4$ is hydrogen, alkyl, cycloalkyl, aralkyl, phenyl, or an alkoxyphenyl group containing up to 10 carbon atoms,
$R^A$ is F, Cl, Br, I, $NO_2$, $NR^{13}R^{14}$, $NHCOR^{13}$, CN, $COOR^{13}$, $OR^{13}$, $SCH_3$ or $SO_2NR^{11}R^{12}$; wherein $R^{13}$ and $R^{14}$ each is hydrogen or alkyl containing up to 6 carbon atoms and optionally substituted with hydroxy or halogen (F, Cl, Br, I) and wherein $R^{11}$ and $R^{12}$ are as defined above
and wherein there may be 1–4 identical or different $R^A$s; and
$R^9$ is hydrogen, alkyl or alkoxycarbonyl each of the latter two containing up to 8 carbon atoms;
with the provisos:
that $R^{11}$ and $R^{12}$ cannot both be hydrogen, when X is oxygen and $R^4$, $R^A$ and $R^9$ each is hydrogen,
that one of the substituents $R^{11}$ and $R^{12}$ cannot be hydrogen when the other is amino and when X is oxygen and $R^4$, $R^A$ and $R^9$ each is hydrogen, and
that $R^4$, $R^A$ and $R^9$ each cannot be hydrogen when X is oxygen and $R^3$ is $OCH_3$.

The class of compounds represented by the above formula are described as being able to displace flunitrazepam from benzodiazepine receptors, and in contrast to benzodiacepine, chlordiacepoxide and diazepam to inhibit aggression without causing impaired motor coordination, which means that the compounds represented by the above formula are suitable for use as non sedating anticonvulsants, antiaggressives and anxiolytics or for stress protection. As such, they can be used for treatment of the following indications:
anxiety and tension conditions, with and without depressions, unrest, and disturbances resulting from stress situations or excess of stimulations, as well as pathological aggressiveness.

SUMMARY OF THE INVENTION

It is an object of this invention to provide a subclass of such compounds having especially valuable properties.

Surprisingly it has now been found that a small group of compounds belonging to the above class but not specifically disclosed in the above mentioned patent application are strong antagonists of benzodiazepines as measured by their lack of benzodiazepine-like pharmacological effects in spite of their high affinity for the benzodiazepine receptors, and their ability to suppres effects of benzodiazepines. These characteristics make the compounds of this invention extremely useful, for example in controlling and adversing the pharmacological effects resulting from treatment with benzodiacepines and other compounds acting through their affinity for the benzodiazepine receptors.

The compounds of the invention are β-carboline-3-carboxylic acid derivatives of the formula

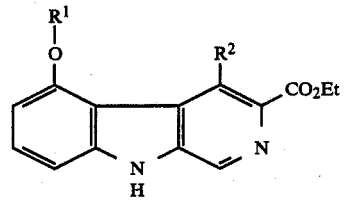

wherein
$R^1$ is methyl, ethyl, n-propyl or iso-propyl, and
$R^2$ is hydrogen, methyl, ethyl, n-propyl or iso-propyl, provided that $R^1$ is not methyl, when $R^2$ is hydrogen.

DETAILED DISCUSSION

The compounds of this invention may be prepared by cyclization of an indole derivative of the formula,

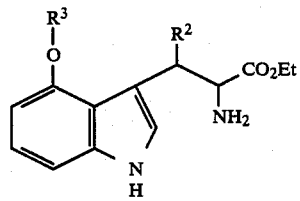

wherein

R[2] is hydrogen, methyl, ethyl, n-propyl or iso-propyl and

R[3] is hydrogen, methyl, ethyl, n-propyl or iso-propyl, provided that R[3] is not methyl, when R[2] is hydrogen, with glyoxylic acid or formaldehyde and thereupon dehydrogenating the intermediarily obtained 1,2,3,4-tetrahydrocarboline derivative and if R[3] is hydrogen followed by etherification of the hydroxyl group by reaction with a compound of the general formula R[1]X, wherein R[1] is methyl, ethyl, n-propyl or iso-propyl and X represents a halogen atom.

The compounds of this invention can be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxyethoxylated castor oil.

Ampoules are conveniently unit dosages.

For oral application, particularly suitable are tablets, dragees, or capsules having talc and/or a carbohydrate carrier or binder or the like, the carrier preferable being lactose and/or corn starch and/or potato starch. A syrup, elixir or the like can be used wherein a sweetened vehicle can be employed.

Generally, the compounds of this invention are dispensed in unit dosage form comprising 0.05–100 mg in a pharmaceutically acceptable carrier per unit dosage.

The dosage of the compounds according to this invention is 0.1–300 mg/day, preferably 1–30 mg/day, when administered to patients, e.g. humans, as a drug.

It is well known (Squires, R. F. and Braestrup, C., Nature (London) 266 (1977) 734) that specific sites in the central nervous systems of vertebrates exhibit a high specific affinity for binding 1,4- and 1,5-benzodiazepines. These sites are called benzodiazepine receptors.

The pharmaceutical properties of the compounds of the invention have been investigated by determining their capability for displacing radioactively labelled flunitrazepam from such benzodiazepine receptors, and their ability to antagonize pentazole induced convulsions.

The displacement activity of the compounds of the invention has been determined by determining the $IC_{50}$ value and $ED_{50}$ value.

The $IC_{50}$ value represents the concentration which causes a displacement of 50% of the specific binding of $^3H$-flunitrazepam (1.0 nM, 0° C.) in samples comprising a total volume of 0.55 ml of a suspension of brain membrane, e.g. from rats.

The displacement test is performed as follows:

0.50 ml of a suspension of non-treated rat forebrain in 25 mM $KH_2PO_4$, pH=7.1 (5–10 mg tissue/sample) is incubated for 40–60 minutes at 0° C. together with $^3H$-diazepam (specific activity 87 Ci/mmol, 1.0 nM) or $^3H$-flunitrazepam (specific activity 87 Ci/mmol, 1.0 nM). After incubation the suspension is filtered through "Whatman GF/C" glass fibre filters, the residue washed twice with cold buffer solution and the radioactivity measured by scintillation counting.

The test is repeated except that prior to the addition of the radioactive labelled benzodiazepine a given amount or an excessive amount of the compound, the displacement capability of which is to be determined, is added. Based on the data obtained the $IC_{50}$ value can be calculated.

The $ED_{50}$ value represents the dose (mg/kg) of a test substance which causes the specific binding of flunitrazepam to benzodiazepine receptors in a living brain to be reduced to 50% of the control value. Such an in vivo test is carried out as follows:

Groups of mice are injected with the test substance at different doses and usually subcutaneously. 15 minutes later $^3H$-flunitrazepam is giving intravenously to the mice and after further 20 minutes the mice are killed, their forebrain membranes is measured by scintillation counting. The $ED_{50}$ value is determined from dose-response curves.

The antagonism of pentazole induced convulsions was investigated.

The test has been performed according to known test models in pharmacology, e.g., as described in R. A. Turner, Screening Methods in Pharmacology, Academic Press, N.Y. and London 1965, esp. p. 164 ff. or Woodbury, P. M., Perry, I. K. and Schmidt, R. P. Antiepileptic Drugs, Raven Press, N.Y. 1972.

The inhibition of motor coordination in mice was also studied 30 minutes after subcutaneous administration in accordance with a method described in the litterature (Buus Lassen et al., Acta Pharmacol. et Toxicol., 1971, 39, 1–16).

Test results obtained by testing some of the compounds of the invention will appear from the following table 1.

TABLE 1

Test substances $R^1O$—[benzene ring]—N(H)—[ring]—$R^2$, CO₂Et position

| $R^1$ | $R^2$ | Inhibition of H³—flunitrazepam binding in vitro IC₅₀ ng/ml | in vivo ED₅₀ mg/kg | Antagonism of pentazole-induced convulsions ED₅₀ i.p. mg/kg | Ataxia (motor-incoordination) |
|---|---|---|---|---|---|
| (CH₃)₂CH | CH₃ | 0.6 | 0.3 | >100 | >100 |
| CH₃ | CH₃CH₂ | 1.4 | 3.0 | >100 | >100 |
| (CH₃)₂CH | H | 0.4 | 6.4 | >100 | >100 |
| Diazepam ("Stesolid" ® )* | | 3 | 1.5 | 3 | 3 |
| Lorazepam ("Temesta" ® )* | | 1 | 0.2 | 0.1 | 0.3 |

*Administered as commercial injection preparations.

All compounds of this invention have affinity for benzodiazepine receptors. Consequently, they have a spectrum of the activities of the benzodiazepines, e.g., muscle relaxant, sedative, anxiolytic or anticonvulsant, the activities being from agonistic to antagonistic to inverse agonistic in each case. The type and level of activity for a given dosage of each compound can be conventionally determined by routine experimentation using well known pharmacological protocols for each of the activities.

It can be seen from the above data that the compounds of this invention very effectively displace ³H-flunitrazepam from the benzodiazepine receptors although they have no antagonizing effect at all against pentazole-induced convulsions and do not possess ataxia properties which means that the compounds of this invention do not possess for example the normal anticonvulsive, anxiolytic and sedative effects of benzodiazepines, thus being antagonists of said benzodiazepines. (A. S. Lippa, P. A. Nash and E. N. Greenblatt in "Anxiolytics", S. Fielding and H. Lal, Futura Publishing Co., Inc., New York 1979). Consequently, the compounds of this invention are particularly useful as agents to reverse the effects of benzodiazepines, especially in cases of overdosage. They are also useful as vigilance enhancers.

The antagonizing effect of the compounds of this invention is further illustrated by testing the effect of one of the compounds of this invention, ethyl 5-isopropoxy-4-methyl-β-carboline-3-carboxylate, against benzodiazepine action in the two in vivo tests of the above table, pentazole-induced convulsions and ataxia. Antagonism of Benzodiazepine action on pentazol-induced seizures in NMRI mice (20–25 g).

5 mg/kg diazepam, administered intraperitoneally 30 minutes before pentazole, totally inhibit the seizures induced by a supramaximal dose of pentazole (150 mg/kg, administered subcutaneously).

The ability of the compounds of this invention to antagonize the effect of benzodiazepine on pentazole-induced seizures has been determined by determining the ED₅₀-value. The ED₅₀-value represents the concentration of the test compound at which clonic seizures were observed in 50% of the animals treated with 5 mg/kg diazepam 30 minutes before the administration of pentazole and the test compound 15 minutes before the administration of pentazole. The test was performed as follows:

At least 4 groups of mice (10 mice in each group) were injected intraperitoneally with 5 mg/kg diazepam. 15 minutes later each group of mice were injected intraperitoneally with different doses of the test compounds and after further 15 minutes the mice received 150 mg/kg pentazol, administered subcutaneously. Clonic seizures within the next 30 minutes were noted. Based on the data obtained the ED₅₀ value was calculated.

In this test the ED₅₀-value of ethyl 5-isopropoxy-4-methyl-β-carboline-3-carboxylate was 0.7 mg/kg. Antagonism of benzodiazepine action in motor incoordination.

NMRI mice (20–25 g) were placed on a horizontal wooden rod (diameter 4.3 cm), rotating at a rate of 6 min⁻¹, 8 cm above the bench. An intraperitoneally injection of 2 mg/kg lorazepam 30 min before test induced ataxia in all animals, defined as more than three falls from the rod within 2 min. The ability of the compounds of this invention to antagonize the effect of benzodiazepine in motor coordination has been determined by determining the ED₅₀-value. The ED₅₀-value represents the concentration at which ataxia were observed in 50% of the animals treated with the test compounds 15 minutes after an intraperitoneally injection of 2 mg/kg lorazepam. The test was performed as follows:

At least 3 groups of mice (8 mice in each group) were injected intraperitoneally with 2 mg/kg lorazepam. 15 minutes later each group of mice were injected with different doses of the test compounds and after further 15 minutes the test for ataxia was performed. Based on the data obtained the ED₅₀-value was calculated.

In this test the ED₅₀-value of ethyl 5-isopropoxy-4-methyl-β-carboline-3-carboxylate was 1.0 mg/kg.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5-isopropoxy-4-methyl-β-carboline-3-carboxylic acid ethylester

A. 5-isopropoxy-3-ethoxycarbonyl-4-methyl-1,2,3,4-tetrahydro-β-carboline-1-carboxylic acid To a stirred solution of 27.25 g 2-amino-3(4-isopropoxyindole-3-yl)butanoic acid ethylester in 70 ml ethylacetate was added 9.99 g glyoxylic acid hydrate dissolved in 70 ml water. The mixture was adjusted to pH 4 (10% K₂CO₃-solution) and further stirred at room temperature for 6 hours. The yellow precipitate was collected by filtration, washed with ethylacetate and dried.

The organic phase from the filtrate was collected, then dried (Na$_2$SO$_4$) and evaporated.

The resulting crude material, 28.6 g (m.p. 126°–130° C. decomp.), was used without further purification.

B. 5-isopropoxy-4-methyl-β-carboline-3-carboxylic acid ethylester 20.3 g of 5-isopropoxy-3-ethoxycarbonyl-4-methyl-1,2,3,4-tetrahydro-β-carboline-1-carboxylic acid was refluxed in 450 ml xylen for 3.5 hours. The mixture was evaporated to give a yellow oil, which was dissolved in 250 ml DMSO. To the solution was added 3.6 g of sulphur and the mixture was stirred at 140° C. for a total of 1.5 hours.

The solvent was evaporated and the residue was purified on SiO$_2$ with hexane—acetone 1+1.

The yield was 8.47 g of 5-isopropoxy-4-methyl-β-carboline-3-carboxylic acid ethylester (m.p. 170°–172° C.).

In a similar way the following compounds were prepared from different tryptophan derivatives.

4-Ethyl-5-methoxy-β-carboline-3-carboxylic acid ethylester, m.p 166°–167° C.

5-Isopropoxy-β-carboline-3-carboxylic acid ethylester, m.p. 209° C.

EXAMPLE 2

5-Isopropoxy-4-methyl-β-carboline-3-carboxylic acid ethylester 0.5 g of 5-hydroxy-4-methyl-β-carboline-3-carboxylic acid ethylester was refluxed in 50 ml ethanol with 0.25 g 2-bromopropane and 0.5 g K$_2$CO$_3$ for 4 hrs. under N$_2$-atmosphere. The mixture was filtrated and evaporated. The resulting residue was purified on SiO$_2$ with dichloromethane—ethanol 1000+25.

The yield was 0.243 g of 5-isopropoxy-4-methyl-β-carboline-3-carboxylic acid ethylester (m.p. 170°–172° C.).

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A β-carbolin-3-carboxylic acid of the formula

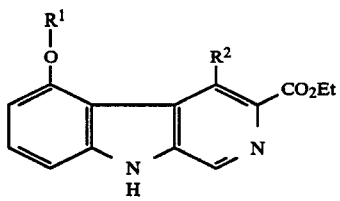

wherein
R$^1$ is methyl, ethyl, n-propyl or iso-propyl, and wherein
R$^2$ is hydrogen, methyl, ethyl, n-propyl or iso-propyl, provided that R$^1$ is not methyl, when R$^2$ is hydrogen.

2. A compound according to claim 1 which is ethyl 5-isopropoxy-4-methyl-β-carbolin-3-carboxylate.

3. A compound according to claim 1 which is ethyl 4-ethyl-5-methoxy-β-carbolin-3-carboxylate.

4. A compound according to claim 1 which is ethyl 5-isopropoxy-β-carbolin-3-carboxylate.

5. A pharmaceutical composition comprising a compound of claim 1 in an amount effective for producing a benzodiazepine antagonist effect and a pharmaceutically acceptable carrier.

6. A method of producing a benzodiazepine antagonistic effect in a patient an in need of such treatment comprising administering to the patient an amount of a compound of claim 1 effective for producing said benzodiazepine antagonistic effect.

7. A compound of claim 1, wherein R$^2$ is methyl, ethyl, n-propyl or iso-propyl.

8. A composition of claim 5, wherein the amount of said compound is 0.05–100 mg.

9. A method of claim 6, wherein said patient is administered a dosage of said compound of 0.1–300 mg/day.

10. A method of claim 6, wherein said patient is administered a dosage of said compound of 1–30 mg/day.

* * * * *